United States Patent [19]
Samour et al.

[11] Patent Number: 5,968,919
[45] Date of Patent: Oct. 19, 1999

[54] HORMONE REPLACEMENT THERAPY DRUG FORMULATIONS FOR TOPICAL APPLICATION TO THE SKIN

[75] Inventors: Carlos M. Samour, Bedford; Scott F. Krauser, Tyngsboro, both of Mass.; Robert J. Gyurik, Exeter, N.H.

[73] Assignee: MacroChem Corporation, Lexington, Mass.

[21] Appl. No.: 08/953,014

[22] Filed: Oct. 16, 1997

[51] Int. Cl.⁶ .................................................... A61K 31/56
[52] U.S. Cl. ..................... 514/177; 514/467; 514/182; 424/448; 424/449
[58] Field of Search .................................. 514/177, 467, 514/182; 424/448, 449

[56] References Cited

U.S. PATENT DOCUMENTS

| | | |
|---|---|---|
| 4,704,282 | 11/1987 | Campbell et al. . |
| 4,788,062 | 11/1988 | Gale et al. . |
| 4,861,764 | 8/1989 | Samour et al. . |
| 4,883,669 | 11/1989 | Chien et al. . |
| 5,118,676 | 6/1992 | Minaskanian et al. . |
| 5,152,997 | 10/1992 | Ebert et al. . |
| 5,164,190 | 11/1992 | Patel et al. . |
| 5,198,223 | 3/1993 | Gale et al. . |
| 5,236,906 | 8/1993 | Yamamoto . |
| 5,252,334 | 10/1993 | Chiang et al. . |
| 5,314,694 | 5/1994 | Gale et al. . |
| 5,512,292 | 4/1996 | Gale et al. . |
| 5,518,734 | 5/1996 | Stefano et al. . |

OTHER PUBLICATIONS

Samour, et al., Proc. Int. Symp. Control. Rel. Bioact. Mater. 16:183–184 (1989).
Marty, et al., Proc. Int. Symp. Control. Rel. Bioact. Mater. 16:179–180 (1989).
Marty, et al., Proc. Int. Symp. Control. Rel. Bioact. Mater. 17:415–416 (1990).
Michniak, et al., Drug Delivery 2:117–122 (1995).
Marty, et al., Abstract of Paper Presented at American Assoc. of Pharmaceutical Scientists, Washington, D.C., Mar. 26–28, 1990.

*Primary Examiner*—James H. Reamer
*Attorney, Agent, or Firm*—Sherman and Shalloway

[57] ABSTRACT

Topical alcoholic or aqueous alcoholic gels containing testosterone, progesterone, estradiol or other hormones have enhanced penetration through skin by including in the formulation 2-n-nonyl-1,3-dioxolane or other hydrocarbyl derivative of 1,3-dioxolane or 1,3-dioxane or acetal, as skin penetration enhancing compound.

17 Claims, 5 Drawing Sheets

HORMONE REPLACEMENT THERAPY DRUG FORMULATIONS FOR TOPICAL APPLICATION TO THE SKIN

FIELD OF INVENTION

This invention relates to topical compositions for transdermal administration of a hormone through the skin of a patient and to the method for transdermally administering the hormone using the topical composition.

DISCUSSION OF THE PRIOR ART

All drugs must be administered in such a manner that they reach the intended site in the body in an optimal concentration (e.g., amount of drug per unit volume of blood) to achieve the desired effect at the proper time, and for an appropriate length of time. Customarily, drugs are taken orally, injected, inhaled, or applied topically. These conventional routes of administration often fail to meet the stated objectives, however. For example, when drugs are absorbed into the blood stream by whatever route, peaks and valleys in the blood concentration of the drug occur and may cause undesirable effects (e.g., peak levels), or loss of activities (e.g., valleys). To meet these problems, a variety of approaches have been investigated. These include, for example, special drug coatings, combining the drug with other materials, suspensions or emulsions, and compressed tablets. Although these formulations attempt to control the release of drugs from their carriers, the desired effects are often not reproducible, may be subject to patient-to-patient variations, and may not be suitable for prolonged periods of delivery, such as days or even months.

Recent research has produced systems in which a drug is implanted in the body, released from skin sites, introduced in to the body by minipumps, and/or released in minute quantities through the skin. These innovative drug-delivery systems are improving drug effectiveness and also are opening opportunities for new pharmaceuticals.

The administration of drugs and other biological materials to the bloodstream via a transdermal route of administration has received much attention in recent years. The skin of an average adult covers more than two square meters of surface area and receives about one-third of all blood circulating through the body. It is elastic, rugged, and generally self-generating. The skin consists of three layers: the stratum corneum (S.C.), the epidermis, and the dermis. The stratum corneum represents the rate-limiting step in diffusion of chemical through the skin. The S.C. is composed of dead, keratinized, metabolically inactive cells which are closely packed together, and consists of an amorphous matrix of mainly lipoid and nonfibrous protein within which keratin filaments are distributed. The cells of the S.C. generally contain 20% water, while the cells below, in the stratum germinativum, contain 70% water. The S.C. does not become hydrated readily. Thus, transdermal permeation is primarily controlled by diffusion through the S.C.

There are several major reasons for the interest in transdermal delivery of drugs:

elimination of uncertainties of absorption from, and irritation to, the gastrointestinal tract which arise when drugs are administered orally.

bypassing the portal circulation, thereby eliminating first-pass metabolism in the liver; this is extremely important for drugs with short half-lives, or with potential unwanted actions on the liver.

delivery of medication directly into the systemic circulation at a constant rate (similar to intravenous infusion).

infrequent dosing (daily, weekly or longer) for certain drugs.

ease of use; foster patient compliance.

However, present transdermal delivery systems often have major drawbacks. For example, they are restricted to low-molecular weight drugs and those with structures having the proper lipophilic/hydrophilic balance. High molecular weight drugs or drugs with too high or low hydrophilic balance often cannot be incorporated into current transdermal systems in concentrations high enough to overcome their impermeability through the stratum corneum.

Transdermal delivery is generally restricted to those medications requiring delivery rates less than 10 mg/day. In order to obtain higher blood levels, the rate of drug delivery must be increased. There have been many proposals to accomplish the higher rate of drug delivery via the use of absorption promoters and by the development of prodrugs that can be more readily absorbed. Examples of existing absorption enhancers include dimethyl sulfoxide (DMSO), ethylene glycol, hexanol, fatty acid and esters, and pyrrolidone derivatives, among others. One such enhancer compound which has received much attention is Azone (N-dodecyl azacycloheptan-2-one).

One of the present applicants has previously developed a new class of compounds which are derivatives of 1,3-dioxanes and 1,3-dioxolanes for use as skin penetration enhancing compounds. These compounds, which have been made commercially available under the trademark SEPA®, are described in detail in U.S. Pat. No. 4,861,764. Work with the dioxolane enhancers has been described in several literature and patent publications. For example, Samour, et al., *Proc. Int. Symp. Control. Rel. Bioact. Mater.* 16: 183–184 (1989); Marty, et al., *Proc. Int. Symp. Control. Rel. Bioact. Mater.* 16:179–180 (1989); Marty, et al., *Proc. Int. Symp. Control. Rel. Bioact. Mater.* 17:415–416 (1990); Michniak, et al., *Drug Delivery* 2:117–122 (1995); Marty, et al., Abstract of Paper Presented at American Association of Pharmaceutical Scientists, Washington, D.C., Mar. 26–28, 1990.

In the article by Michniak, et al., the effect of the vehicle selected for the formulation was noted to play a very important role in the optimization of activity. In particular, it was noted that in certain cases propylene glycol was shown to possess a synergistic effect with Azone, depending on the model drug tested.

There have been several disclosures of topical transdermal formulations for delivery of various hormonal compounds, such as testosterone, progesterone, etc., appearing in the patent literature. Representative of these are the following U.S. Pat. Nos.: 5,164,190 (progesterone, testosterone, estradiol); 5,198,223, 5,314,694 (co-administration of estrogen, such as ethinyl estradiol and synthetic 19-nor-progesterone (ST-1435)); 5,236,906 (adrenocortical hormone, e.g., hydrocortisone butyrate, for skin disease); 5,152,997 (testosterone); 4,704,282 (testosterone, progesterone, hydrocortisone); 5,252,234 (estradiol, norethindrone, levonorgesterol); 4,788,062 (progesterone and/or an estradiol ester); 5,512,292 (gestodene and estrogen, e.g., ethinyl estradiol); 5,518,734 (estradiol); 4,883,669 (estradiol). Generally, the topical compositions disclosed in these patents may or do include skin penetration enhancing compounds to promote the penetration of the active hormone compound(s) through the skin.

Other patents representative of use of particular skin penetration enhancing compounds which may possibly be used in combination with hormones or other physiologically active drugs include: U.S. Pat. Nos. 5,118,676 (e.g, 1-N-dodecyl-2-pyrrolidone-5-carboxylic acid, 2-pentyl-2-oxo-pyrrolidineacetic acid, 2-dodecyl-2-oxo-1-pyrrolidineacetic acid, 1-azacycloheptan-2-one)-2-dodecylacetic acid; both open and closed-chain embodiments of the penetration enhancer are stated to be sufficient); 5,482,965 (aminoalcohol derivatives, including derivatives of 1,3-dioxanes).

While there are many prior art patent and literature disclosures of topical hormone delivery systems, including, for examples, formulations for topically delivering testosterone, there has not, to date, been any commercially available non-patch topical testosterone or other hormone products. Other topical hormone products are still not sufficient. There are however, a few commercially available transdermal hormone delivery patch products which are commercially available, for example, Androderm®, from Theratech and Testoderm®, from ALZA Corp, for testosterone; Estraderm®, from Ciba Pharmaceutical, for estradiol. All of these products which are currently available in the United States are of the infinite dose type in contrast to the European Oestrogel® which is of the finite dose type.

The reasons that commercial topical (e.g., gel, cream, ointment) products have not become readily available or are not entirely satisfactory, are not always known. Undoubtedly, it is the result of several factors. For example, it is believed, in general, that the prior disclosures and attempts to produce topical hormone replacement therapies have not been successful due to the inability to adequately and stably target the intended site with therapeutically effective dosages in a reasonable period of time. In addition, effective carrier systems, including, for example, solvents for the hormonal drug of interest and suitable percutaneous penetration enhancers, having the requisite product stability and drug delivery profiles, generally cannot be developed based simply on the knowledge of carrier systems in topical formulations for other specific drugs or even from the carriers for patch systems from the same drug.

While transdermal patch delivery systems often provide some advantages, they all rely on particular adhesive layers for adhering the patch to the target site and, therefore, for at least some patients, can result in irritation, while for other candidate patients with, for example, excessively oily or tender skin, or for hairy skins, patches may not be applicable. Patch delivery systems differ from topical formulations in that drug delivery with the former is membrane diffusion controlled whereas drug delivery with the latter is thermodynamically controlled.

Therefore, a topical formulation to be applied directly to the skin, in the form of, for example, gel, ointment, or cream, would be highly advantageous. However, to be feasible, such topical formulation should be easy to apply without being too runny, greasy, or otherwise messy to use by the patient. Furthermore, since topical gel formulations, as contemplated herein, provide a finite dose of the medicament, it is necessary to maintain a relatively uniform (e.g., high) flux of the medicament over time even as the concentration of the medicament in the gel decreases over time.

The present invention provides a solution to the above problems using the hydrocarbyl-group substituted 1,3-dioxolanes, 1,3-dioxanes and acetals as skin penetration enhancers (SPE), which have been formulated with carrier systems designed to effectively solubilize both the hormonal drug and the skin penetration enhancer; provide long shelf-life and stability; remain on the skin for extended periods of time; and effectively and consistently provide the desired drug delivery profile for a particular drug and particular patient (e.g., skin type; dosage requirement, etc.); and further, without requiring any particular device or patch or other adhesive based system.

In particular, the present inventors have continued to study the effect of the 1,3-dioxane and 1,3-dioxolane derivatives and related acetals as skin penetration enhancer (SPE) compounds for various hormonal compounds. Surprisingly, it has been found that this class of SPE compounds provides better drug delivery profiles than the commercially available patch systems for hormone replacement therapies. For example, as will be shown in the examples to follow, if the gel from a commercially available patch reservoir system is removed and applied as a finite film on the skin in the same manner as for the topical gels of this invention, the flux of the former is greatly reduced as compared to that of the latter. Accordingly, the gel from the reservoir system would not be effective as a topical product and must be presented as a reservoir system in order to overcome this fundamental drug delivery problem. This then necessitates the application of a patch which must remain in place for prolonged periods, in turn exacerbating such problems as irritation, user non-compliance, and the like. Moreover, delivery may still be less than is attainable by the present gels.

SUMMARY OF INVENTION

The present invention has as a principal object to provide stable topical compositions effective for the transdermal application of testosterone, estradiol, or other hormone compounds by the application of the composition to the skin.

The above and other objects of the invention, which will become more apparent from the following more detailed description and preferred embodiments is achieved, according to a first aspect of the invention, by an hormonal drug containing alcoholic or aqueous alcoholic composition which comprises, on a weight basis, of the total composition:

a therapeutically effective amount of hormonal drug;

a skin penetration enhancing effective amount, in the range of from about 0.5 to 25%, of a $C_7$ to $C_{14}$-hydrocarbyl substituted 1,3-dioxolane, 1,3-dioxane or acetal (which may hereinafter be collectively referred to as SPE);

0 to about 30% of 1,2-diol having from 3 to 6 carbon atoms;

at least about 35% of volatile alcohol selected from the group consisting of ethanol, propanol and mixture thereof;

0 to about 40% water; and, optionally, a gelling agent effective to thicken the composition to avoid or minimize run-off when applied to the skin.

In preferred embodiments of this aspect of the invention the ingredients are included in the formulation in the following ranges:

from about 0.01 to 10%, preferably 1 to 6%, especially preferably 1.0 to 4% hormone;

from about 2 to 15%, preferably 5 to 10% of SPE wherein the hydrocarbyl group substituent has from about 7 to 10 carbon atoms;

from about 5 to 30%, preferably 5 to 20% propylene glycol;

from about 35 to 70% ethanol, isopropanol or mixture thereof;

from about 0 to 35% water; and, up to about 4% of cellulosic thickener.

Furthermore, the formulations according to the invention are preferably further characterized by an average in vitro flux greater than about 5 $\mu g/cm^2/day$, preferably greater than about 10 $\mu g/cm^2/day$ and especially preferably, greater than about 20 $\mu g/cm^2/day$, and usually up to as high as about 40 $\mu g/cm^2/day$.

BRIEF DESCRIPTION OF THE DRAWINGS

FIG. 4-B is a graph plotting Payload (cumulative diffusion) as percent of dose of estradiol versus time for the same samples used in the study of FIG. 4-A.

DETAILED DESCRIPTION AND PREFERRED EMBODIMENTS

Figure 1:
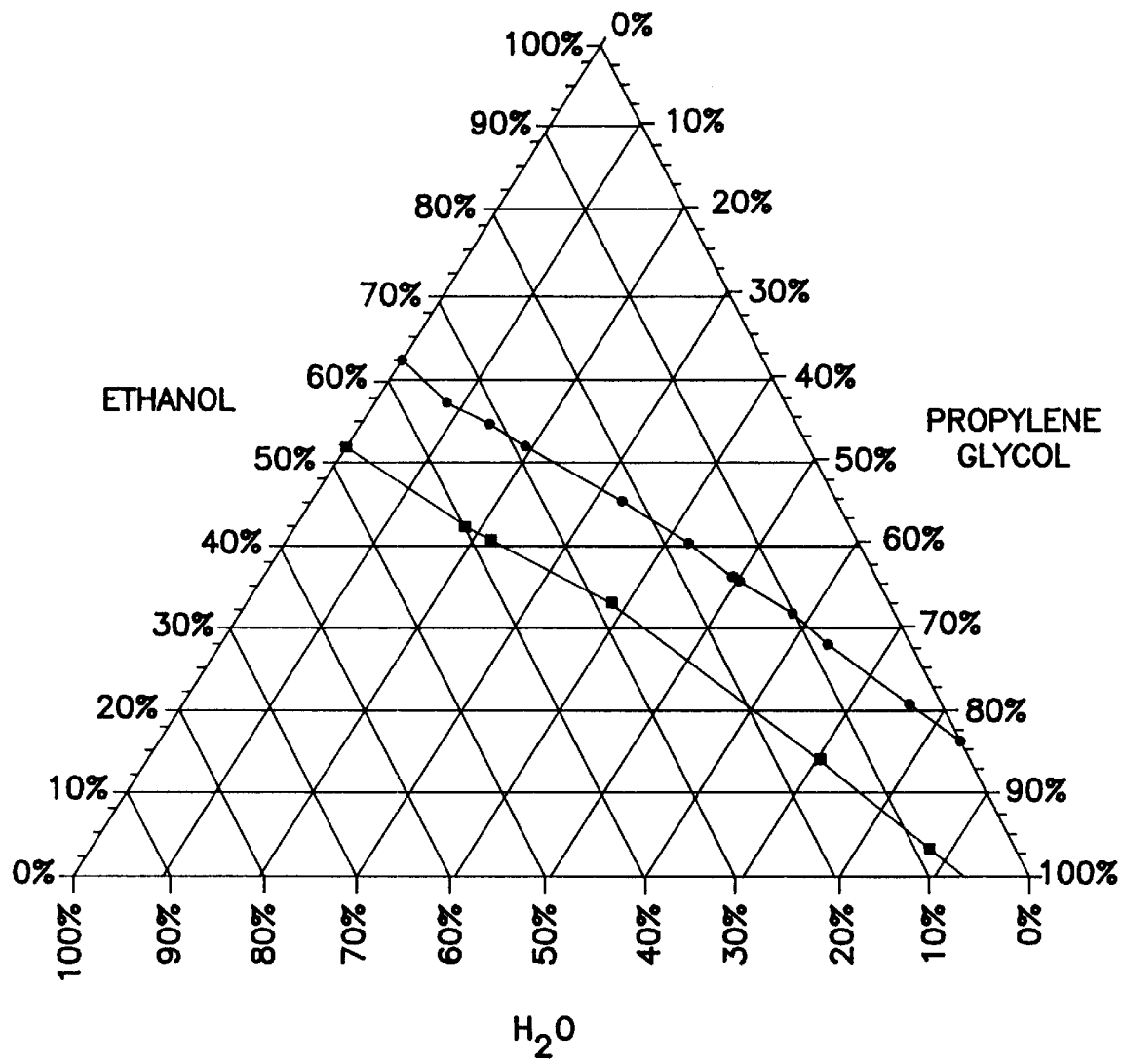
FIG. 1 is a ternary phase diagram showing the miscibility of 2-n-nonyl-1,3-dioxolane skin penetration enhancer in an ethanol-propylene glycol-water vehicle.

The compositions of the invention are intended for topical, non-invasive, application to the skin, particularly to those regions of the skin, e.g., inside arm, back, etc., providing maximal systemic absorption of the hormonal active ingredient.

Examples of the hormonal drug (hormone) which is advantageously administered by the topical formulations of this invention include, for example (with typical indications shown in parentheses) Androgens, such as, for example, androstenediol and androisoxazole (for anabolic disorders), testosterone (hypogonadism, muscle wasting, male impotence, postmenopausal symptoms in women), dihydrotestosterone (hypogonadism, muscle wasting), dehydroepiandrostenone (muscle wasting, fat reduction, fitness); estrogens (postmenopausal symptoms, birth control), such as, for example, 17 beta-estradiol, estradiol-3,17-diacetate, estradiol-3-acetate, estradiol-17-acetate, estradiol-3,17-valerate, estradiol-3-valerate, estradiol-17-valerate, ethinyl estradiol, estrone; progesterones (prevent endometriosis, prevent endometrial cancer, control habitual abortion, suppress or synchronize estrus, promote hair growth), such as, for example, progesterone (preg-4-ene-3,20-dione), norethindrone, norgestrieone, norgestadienone, norgestrel, norgestimate, progestogenic acid, dihydroprogesterol, nomagesterol. Furthermore, in the above listed exemplary hormones, the testosterone hormone may be used in any of its usual forms, such as, for example, acetate, propionate, 17-beta-cyclopentane-propionate, enanthanate, isobutyrate, undeconate, and the like. Similarly, the estradiols may additionally be used in any of the known or newly developed forms, such as, for example, pivalate, propionate, cypionate, benzoate and other esters. Among these, especially preferred, based on the current level of knowledge in the pharmacological arts, are testosterone, progesterone and estradiol, in any of the salt or ester forms.

More generally, however, any of the government approved hormones, such as listed in, for example, the most current edition of The Merck Index, may be advantageously used.

The penetration of the active ingredient through the skin is enhanced to an acceptable level by including in the composition a skin penetration enhancing effective amount of an SPE of the substituted 1,3-dioxacyclopentane and substituted 1,3-dioxacyclohexane types disclosed in U.S. Pat. No. 4,861,764, the disclosure of which is incorporated herein in its entirety by reference thereto, or the corresponding substituted acetal compound. Representative examples of the skin penetration enhancing compounds include:

2-substituted 1,3-dioxolanes of the formula (I):

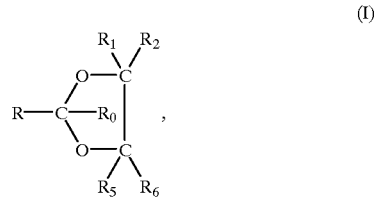

2-substituted 1,3-dioxanes of the formula (II):

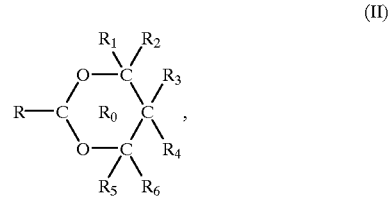

substituted-acetals of the formula (III):

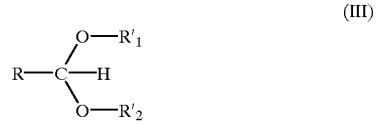

In the above formulas (I), (II) and (III) R preferably represents a $C_7$ to $C_{14}$ hydrocarbyl group, $R_0$, $R_1$, $R_2$, $R_3$, $R_4$, $R_5$, and $R_6$, each, independently, represent hydrogen or a $C_1$ to $C_4$ alkyl group.

$R'_1$ and $R'_2$, each, independently, represent $C_1$ to $C_4$ alkyl group.

The hydrocarbyl group for R may be a straight or branched chain alkyl, alkenyl or alkynyl group, especially alkyl or alkenyl. Preferably, R represents a $C_7$ to $C_{12}$ aliphatic group; especially $C_7$ to $C_{10}$ aliphatic group.

Examples of suitable alkyl groups include, for example, n-heptyl, n-octyl, n-nonyl, n-decyl, n-undecyl, n-dodecyl, 2-methyl-octyl, 4-ethyl-decyl, 8-methyl-decyl, and the like. The straight chain alkyl groups, such as n-heptyl, n-octyl, n-nonyl and n-decyl, are especially preferred. Examples of alkenyl groups include, for example, 2-hexenyl, 2-heptenyl, 2-octenyl, 2-nonenyl, 2',6'-dimethyl-2',6'-heptadienyl, 2'6'-dimethyl-2'heptaenyl, and the like. The R group may also be substituted by, for example, halo, hydroxy, carboxy, carboxamide and carboalkoxy.

The $C_1$ to $C_4$ alkyl group may be, for example, methyl, ethyl, n-propyl, isopropyl, n-butyl, tert-butyl, and the like. The preferred alkyl groups for $R_0$, and for $R_1$ to $R_6$ and for $R'_1$ and $R'_2$ are alkyl having 1 or 2 carbon atoms, most especially ethyl. $R_0$, and $R_1$ to $R_6$ may also, preferably, all be hydrogen.

Specific enhancer compounds include, for example, 2-n-heptyl-1,3-dioxolane, 2-n-nonyl-1,3-dioxolane, 2-n-undecyl-1,3-dioxolane, 2-n-nonyl-1,3-dioxane, 2-n-undecyl-1,3-dioxane, 2-n-heptylaldehyde-acetal, 2-n-octyl-aldehyde-acetal, 2-n-nonylaldehyde-acetal, 2-n-decylaldehyde-acetal, 3,7-dimethyl-2,6-octadienal (citral), citronal and the like. 2-n-nonyl-1,3-dioxolane (2-NND) is especially preferred.

The amount of the enhancer compound is selected to provide the desired delivery rate for the active compound but, taking into consideration such additional factors as, product stability, side effects, carrier system and the like. Generally, depending on the particular hormone and other vehicles, amounts in the range of from about 0.5 to 25%, preferably from about 2 or 3 to 12 or 15 percent, especially from about 5 to 10 percent, of the composition, will provide optimal flux rate and 24 hour payload of the active ingredient.

For any particular formulation the hormone and other ingredients may be selected to achieve the desired drug delivery profile and the amount of penetration desired. The optimum pH may then be determined and will depend on, for example, the nature of the hormone, the base, and degree of flux required. Generally, neutral to slightly basic pH's are preferred.

The compositions are generally formulated as gels, especially aqueous-alcoholic gels. However, other forms, such as, for example, lotions, creams, mousses, aerosols, ointments, etc., may be used so long as when applied to the affected or desired area of the skin the formulation will stay in place, i.e., without run-off, for sufficient time, to permit an individual to spread and retain the composition over and on the skin.

The vehicle for any of the forms of the compositions of the invention will usually include a diol, particularly, a 1,2-diol, such as, for example, 1,2-propylene glycol, 1,2-butylene glycol, 1,2-hexylene glycol, etc., lower alcohol, e.g., ethanol, and/or isopropanol, and, usually, water. A thickening or gelling agent is also usually and preferably included to facilitate application of the formulation to the skin. In addition, of course, the skin penetration enhancing dioxolane, dioxane or acetal is included in the formulations in an amount effective to enhance the penetration of the active hormone ingredient through the skin, including the stratum corneum.

Figure 2:
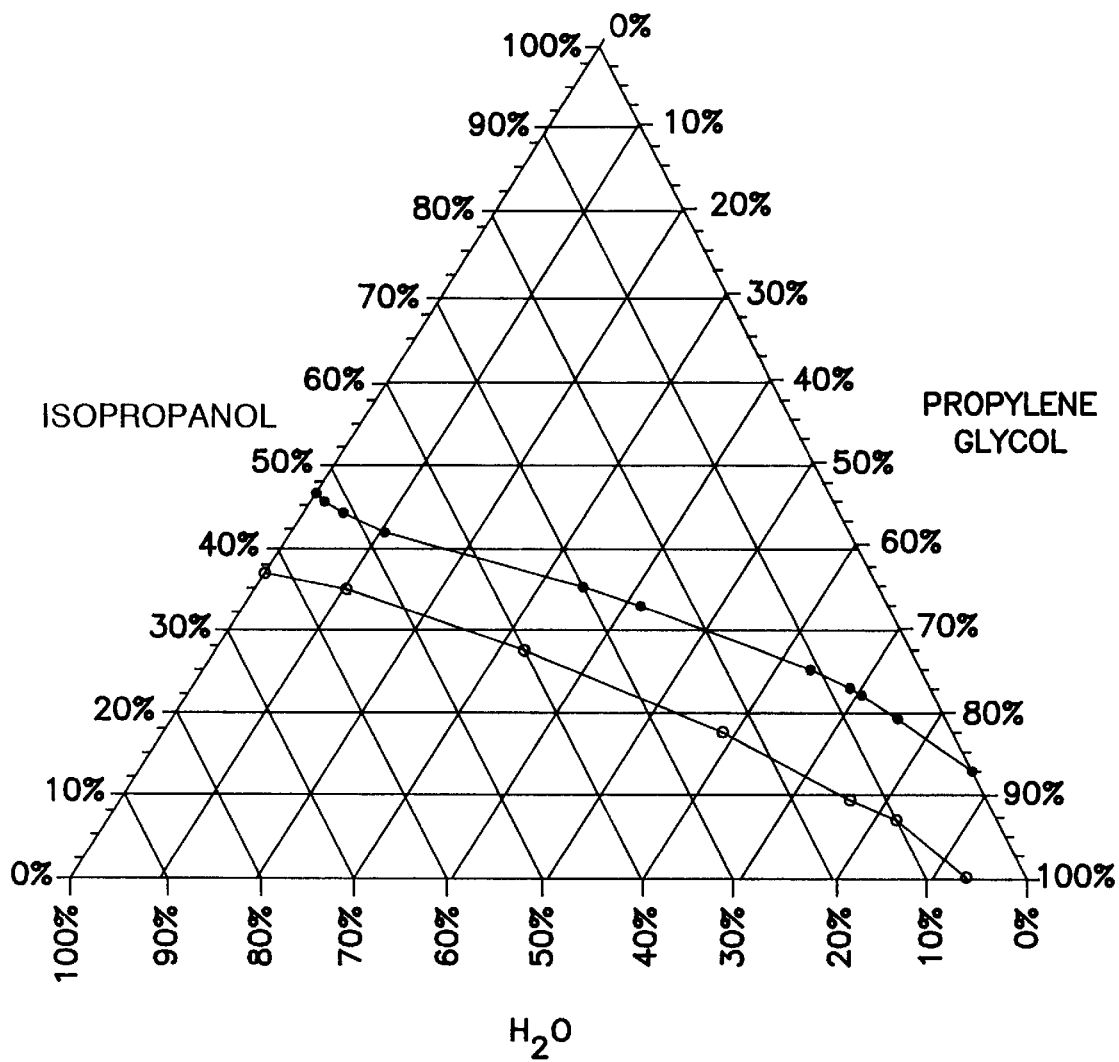
FIG. 2 is a ternary phase diagram showing the miscibility of the 1,3-dioxolane skin penetration enhancer in an isopropanol-propylene glycol-water vehicle.

Accordingly, the vehicle or carrier system for the hormone and enhancer components is preferably an aqueous or non-aqueous alcoholic carrier containing sufficient alcohol, especially ethanol and/or isopropanol and, usually, 1,2-diol, e.g., 1,2-propylene glycol, to solubilize the hormone and be miscible with the SPE. Generally, however, depending on the amounts of SPE and hormone in the formulations the aqueous alcoholic carrier can contain from about 35% to about 70% of ethyl alcohol and/or isopropyl alcohol, preferably, from about 50 to about 70 percent of ethanol or from about 45 to 55 percent of isopropanol. Mixtures of ethanol and isopropanol in proportions providing the desired solubility of hormone and compatibility with the SPE can also be used. More generally, however, the present inventors have developed miscibility data for combinations of alcohol (ethanol or isopropanol), 1,2-diol (1,2-propylene glycol) and water for one specific SPE, namely, 2-n-nonyl 1,3-dioxolane (2-NND). This data is graphically represented by the ternary phase diagrams provided as FIG. 1 (for ethanol) at 2 wt. % (●) and 10 wt. % (■) of 2-NND and FIG. 2 (for isopropanol) at 2 wt. % (○) and 10 wt. % (●) of NND. In each of these phase diagrams, the upper portions (above the lines connecting the data points) represent the proportions at which the vehicle components are miscible with each other and with the SPE; conversely, the region below the lines connecting the data points represent the proportions where the vehicle components are immiscible.

Again, the total amount of the aqueous or non-aqueous, alcoholic carrier will depend on the amount of hormone, amount and type of SPE, and the form of the composition, e.g., gel, cream, ointment, etc. Usually amounts of the aqueous or non-aqueous alcoholic carrier within the range of from about 70% to about 95% may be used.

In the preferred compositions which are in the form of a gel, a thickening agent, such as hydroxypropyl cellulose, will be included as a gelling agent. However, any other pharmaceutically acceptable thickening/gelling agent may be used. For example, mention may be made of other cellulosic ethers, polymeric thickening agents, e.g., acrylic acid polymers, Carbopol® thickeners, etc., xanthan gum, guar gum, and the like, as well as inorganic thickeners/gelling agents. The amount of the thickening agent is not particularly critical and can be selected to provide the desired product consistency or viscosity to allow for easy application to the skin but which will not be too watery or loose so that it will stay where applied. Generally, depending on its molecular weight, amounts of thickening agent up to about 5%, such as, for example, from 0.1 to about 2%, of the composition will provide the desired effect.

As is also well known in this art, it is possible to include other ingredients in the formulations for particular aesthetic and/or functional effects. For example, the formulations may, optionally, include one or more moisturizers for hydrating the skin and emollients for softening and smoothing the skin. Glycerin is an example of such a suitable moisturizing additive. When present the additive will usually be incorporated in an amount of up to about 5 percent by weight of the composition, for example, from about 0.1 to 5%.

The effects of the topical compositions according to the invention are further illustrated by way of the following representative examples which in no way are intended to limit the scope of the invention.

EXAMPLE 1

This example compares the percutaneous absorption through human skin of progesterone (preg-4-ene-3,20-dione) from aqueous alcoholic gels or solutions containing from 1 to 6 wt. % progesterone and 0 or 5%, 10% or 15% of 2-n-nonyl-1,3-dioxolane (2-NND), using an ethanol/propylene glycol/water carrier at a 70:20:10 mixing ratio (except as noted). Hydroxypropyl cellulose (2 wt. %) is used as the gelling agent in the gel formulations. The test compositions are applied to provide about 30 milligrams (mg) of the composition per square centimeter (cm$^2$) of human skin.

The tests are run in standard static cells with phosphate buffered saline (PBS) and ethanol mixture (80:20) as the receptor fluid (surface area 0.635 cm$^2$, temperature 32° C.). The following Table 1 shows the total amount of progesterone, enhancer (2-NND), ethanol (E), 1,2-propylene glycol (PG) and water for each formulation.

Each test was run for 24 hours under non-occluded conditions with the finite dose of the test formulation.

TABLE 1

| Run No. | Type | Progesterone wt. % | 2-NND wt. % | Peak Flux μg/cm$^2$/hr | 24 hour %-dose |
|---|---|---|---|---|---|
| 1 | gel | 2 | 0 | 1.9 | 10 |
| 2 | gel | 2 | 0 | 6 | 6 |
| 3 | solution | 6 | 0 | 8 | 8 |
| 4 | gel | 2 | 5 | 4 | 7.5 |
| 5 | gel | 1 | 5 | 3.6 | 9 |
| 6 | gel | 2 | 5 | 3.2 | 8.8 |
| 7 | solution | 2 | 5 | 2.3 | 8 |
| 8 | solution* | 2 | 10 | 4 | 13 |
| 9 | gel | 2 | 10 | 8 | 17 |
| 10 | solution | 2 | 10 | 5 | 14 |
| 11 | solution | 4 | 10 | 7 | 12 |
| 12 | solution | 6 | 10 | 4.2 | 2.9 |

*Ethanol/PG/Water mixing weight ratio 70:10:20.

EXAMPLE 2

This example compares the percutaneous absorption of progesterone through human skin from 1% or 2% gel formulations with and without skin penetration enhancer (2-n-nonyl-1,3-dioxolane,2-NND) in the aqueous alcoholic gel formulation using ethanol:propylene glycol:water vehicle at a 70:20:10 or 70:10:20 weight mixing ratio. The compositions used in these tests are shown in the following Table 2. Hydroxypropyl cellulose (2 wt. %) is used as the gelling agent in the gel formulations. The test compositions are applied to provide about 30 milligrams (mg) of the composition per square centimeter (cm$^2$) of human skin.

The tests are run in standard static cells with phosphate buffered saline (PBS) and ethanol mixture (80:20) as the receptor fluid (surface area 0.635 cm$^2$, temperature 32° C.).

TABLE 2

| | progesterone (%) | 2-NND (%) | Vehicle (%) | Vehicle Composition | peak flux μg/cm$^2$/h | % of dose 24 hr |
|---|---|---|---|---|---|---|
| 1 | 2 | 0 | 98 | 70:20:10 EtOH/PG/H2O | 4.3 | 2.48 |
| 2 | 2 | 5 | 93 | 70:20:10 EtOH/PG/H2O | 4.4 | 14.07 |
| 3 | 2 | 5 | 93 | 70:10:20 EtOH/PG/H2O | 4.2 | 13.22 |
| 4 | 1 | 5 | 94 | 70:20:10 EtOH/PG/H2O | 3.6 | 9.00 |

EXAMPLE 3

This example is similar to Example 2 but comparing formulations with 2% progesterone and either 10% of enhancer (2-NND) or without enhancer in aqueous gel formulations containing Ethanol:PG:Water carrier at a 70:20:10 mixing weight ratio. The test conditions are, otherwise, the same as described in Example 2. The tested formulations and results are shown in Table 3.

TABLE 3

| # | Enhancer (2-NND) (%) | Peak Flux μg/cm$^2$/hr | 24 Hour Percent of Dose |
|---|---|---|---|
| 1 | 0 | 6 | 6 |
| 2 | 10 | 8 | 17 |

EXAMPLE 4

This example shows the results for a topical aqueous alcoholic gel formulation according to the present invention for the transdermal delivery of estradiol in comparison to the formulation of a commercially available estradiol-containing patch. The topical gel according to the present invention contained 0.06% estradiol whereas the patch formulation contained 0.1 wt. % estradiol. The tests were run under the same conditions as described in Example 2.

In this example the "patch" formulation was obtained from an Estraderm® 0.1 patch which nominally delivers 100 micrograms of estradiol per day when applied twice per week. An appropriate amount of gel was removed from the Estraderm patch and used in the tests. The results for cumulative delivery of the patch formulation for 24 hours is calculated on the basis of 3.5 day delivery per patch. Although the patch is designed to meter the dose over the desired period (3.5 days) via an attenuating membrane, in the subject in vitro tests on human skin, the gel was applied without the membrane component of the Estraderm patch. All of the gels were essentially depleted of estradiol within 24 hours as apparent from the flux at 24 hours<0.5 μg/cm$^2$/hr. The results obtained from the static cell in vitro tests run under the same conditions as previously described are shown in the following Table 4:

TABLE 4

| Estradiol Formula | Peak Flux μg/cm$^2$/hr | Cumulative delivery at 24 hr. μg/cm$^2$ | Cumulative delivery at 24 hr. μg | Cumulative amount at 24 hr. % of dose |
|---|---|---|---|---|
| Invention: 0.06% drug 5% 2-NND E:PG:W = 70:20:10 | 0.2 | 2.0 ± .5 | 1.3 ± 0.3 | 10.4 ± 2.1 |
| Estraderm, non-occluded | 0.3 | 2.8 ± 1.4 | 1.8 ± 0.9 | 0.6 ± 0.3 |
| Estraderin, occluded | 3.0 | 23.8 ± 6.1 | 15.1 ± 3.9 | 4.4 ± 1.1 |

In the above Table 4 the non-occluded Estraderm gel was used without the protective cover layer provided with the commercial product, whereby the volatile solvents are allowed to evaporate. In the occluded Estraderm gel the protective cover layer was maintained over the gel to inhibit evaporation of the volatile solvents.

The following Table 5 provides a comparison between the obtained and expected results for the Estraderm gel (occluded) and the gel of the present invention by taking into consideration the actual patch delivery area (20 cm$^2$) and the recommended 3.5 day (2 per week) patch delivery cycle.

TABLE 5

|  | Estraderm (occluded) | Invention Gel |
|---|---|---|
| Estradiol (%) | 1.8 | 0.06 |
| Amount Applied (mg gel/0.635 cm$^2$) | 20.13 | 20.19 |
| Amount Applied, this study (mg gel/cm$^2$) | 31.7 | 31.8 |
| Amount Applied, intended (mg gel/cm$^2$) | 22.3 | 10.0 |
| In Vitro Transdermal Delivery ($\mu$g/cm$^2$/24 h)$^\#$ | 23.8 | 2.0 |
| 84 or 24 hr Amt delivered ($\mu$g(est.)/20 cm$^2$) | 475.4 | 40.0 |
| 24 hr Amt delivered ($\mu$g(est.)/20 cm$^2$) | 135.8 | 40.0 |
| Adjusted 24 hr Amt. delivered ($\mu$g(est)/20 cm$^2$)* | 95.5 | 40.0 |
| Equivalent Amt. delivered IF: (1.0 g. Invention Gel/100 cm$^2$) | — | 62.9 |
| Amt (g) of Invention Gel to apply to deliver 50 $\mu$g/day | — | 0.8 |
| Amt (g) of Invention Gel to apply to deliver 100 $\mu$g/day | — | 1.6 |
| Reported Delivery (Estraderm Product Brochure) | 350 | — |
| Observed delivery, 3.5 days, this study | 334 | — |
| Equivalent coverage area (cm$^2$) | 20 | 100 |

$^\#$ = as found in this study
* = Difference in formulation amt. applied, Patch in vivo vs. this study From the above results it may be appreciated that the gel formulation according to the present invention is substantially as or more effective as the commercially available reservoir patch estradiol product while providing ease of use, increased flexibility of use, less irritation and substantially lower cost based on active ingredient.

EXAMPLE 5

This example compares the results of the same aqueous alcoholic topical gel estradiol formulation according to the present invention as used in Example 4 versus a control gel without the enhancer and a commercially available gel product, Oestragel®.

Figure 3:
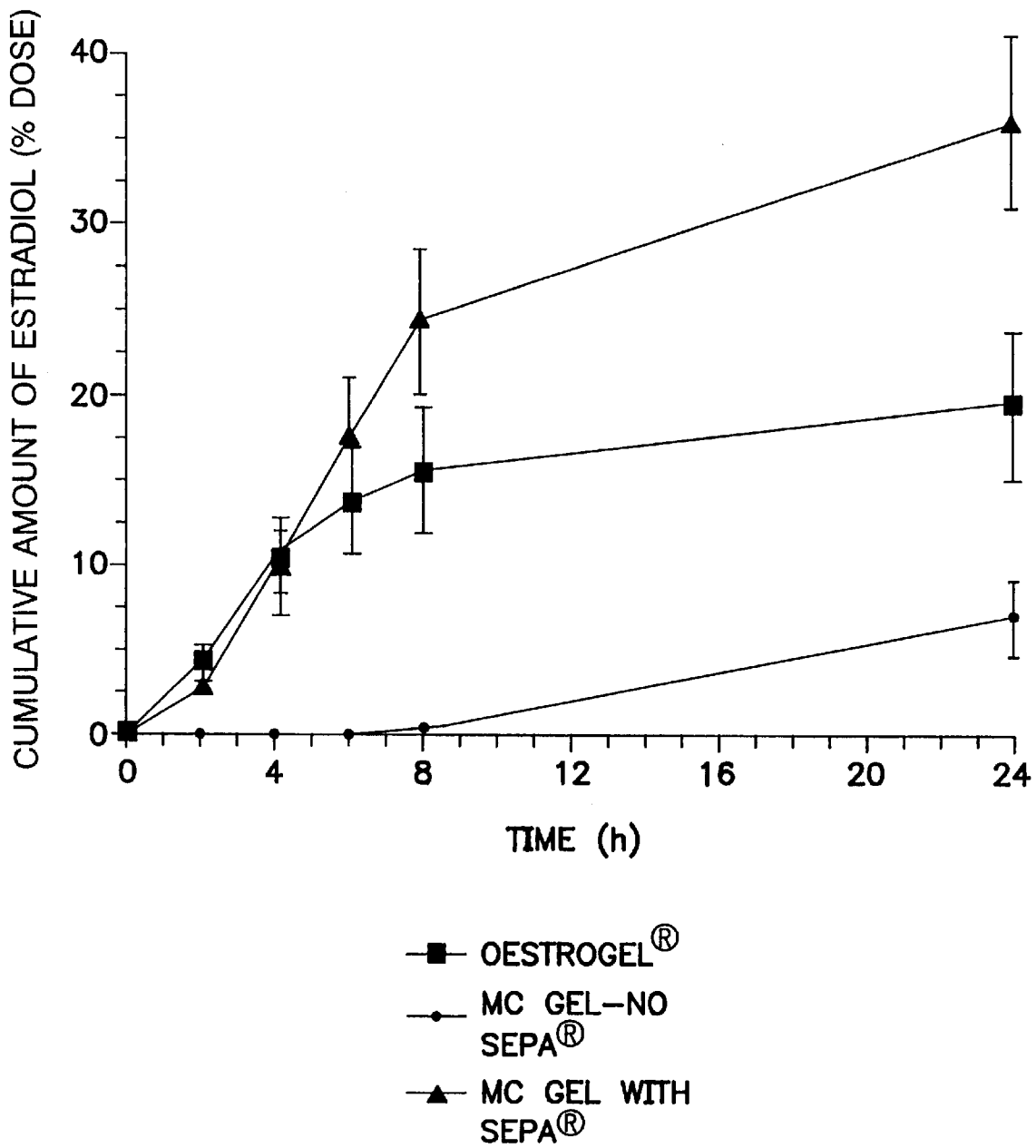
FIG. 3 is a graph plotting the cumulative absorption of estradiol, as percent of dose versus time, from a gel according to the invention (▲), a similar gel but without the skin penetration enhancer (●); or from a commercial product (■).
Figure 4A:
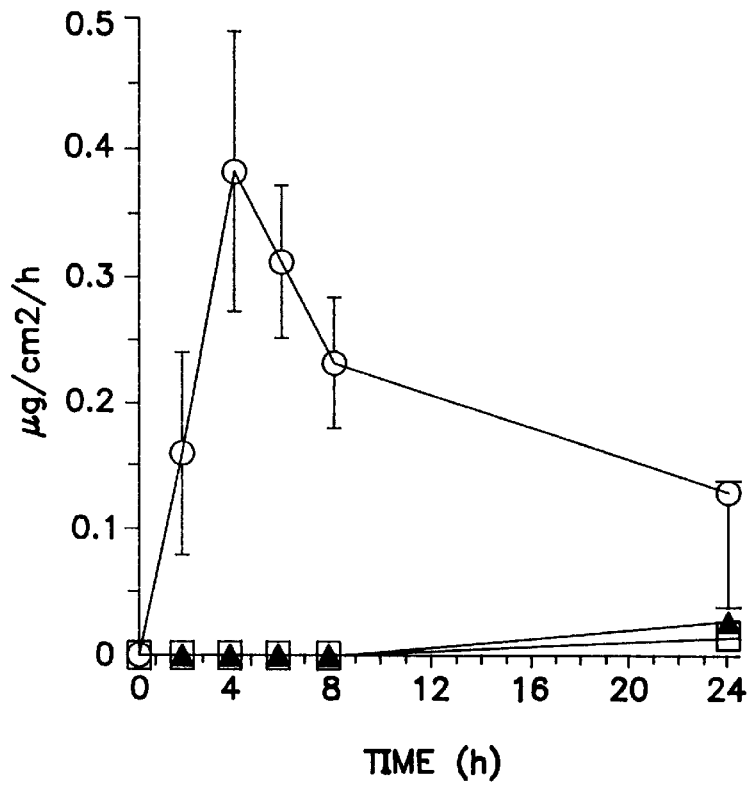
FIG. 4-A is a graph plotting flux of estradiol versus time in an in vitro study for an aqueous alcoholic gel according to the invention containing 2 wt. % estradiol, and 10 wt. % of 2-n-nonyl-1,3-dioxolane (2-NND) skin penetration enhancer (○), or a similar control gel containing 2 wt. % estradiol but without skin penetration enhancer (□), or a similar gel containing 2 wt. % estradiol and 10 wt. % of a different skin penetration enhancer, laurocapram (Azone®) (▲).
Figure 4B:
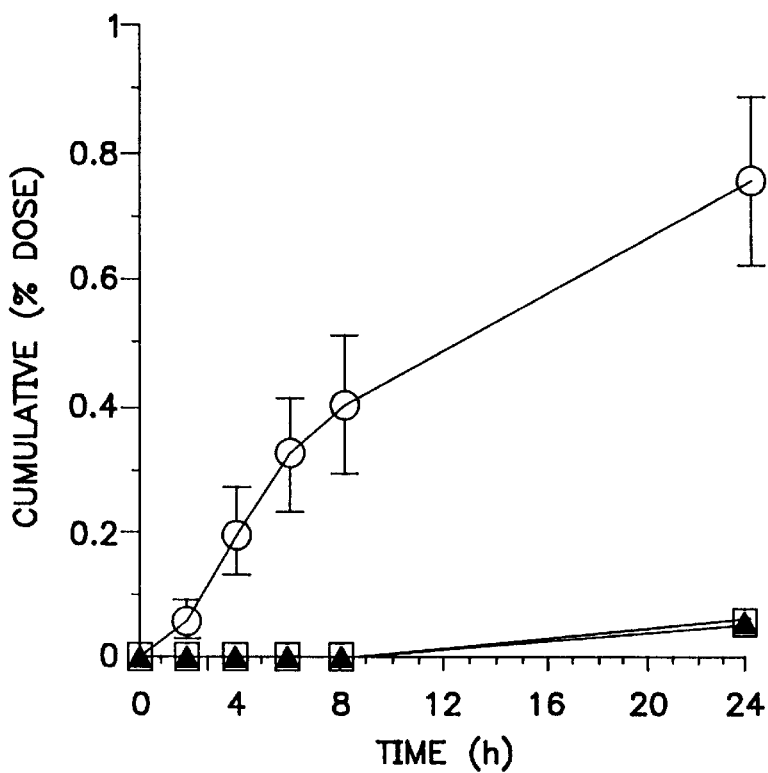

The results are shown in FIG. 3 for cumulative amount of estradiol diffused through the human skin sample as a function of time. The cumulative amount of the estradiol is significantly higher for the invention formulation than for the control or commercial product.

EXAMPLE 6

This example is designed to compare the influence of various glycol coenhancers on the percutaneous absorption of hormone (estradiol) using the following formulation:

| Ingredient | wt. % |
|---|---|
| Estradiol | 2 |
| 2-NND | 10 |
| Ethanol (70% aq.) | 68 |
| Glycol Coenhancer | 20 | in in vitro tests on human skin using the same test cells as described in Example 1. The results are shown in the following Tables 6 and 7.

TABLE 6

| Run No. | Coenhancer | % of dose delivered at 24 hr. |
|---|---|---|
| 1 | 1,2-butylene glycol | 2.78 |
| 2 | 1,2-hexylene glycol | 2.01 |
| 3 | 1,2-propylene glycol | 1.88 |
| 4 | 1,3-propylene glycol | 1.21 |
| 5 | Ethylene glycol | 0.97 |
| 6 | 1,2-dodecanediol | 0.90 |

TABLE 7

| Run No. | Coenhancer | % of dose delivered at 24 hr. |
|---|---|---|
| 1 | 1,2-propylene glycol | 1.68 |
| 2 | Glycerol (1,2,3-proopanetriol) | 0.45 |

Table 6 shows the superior performance of 1,2-diols having from 3 to 6 carbon atoms. Table 7 shows the superior performance of the 1,2-diol as compared to a triol with the same number of carbon atoms.

EXAMPLE 7

Figure 5:
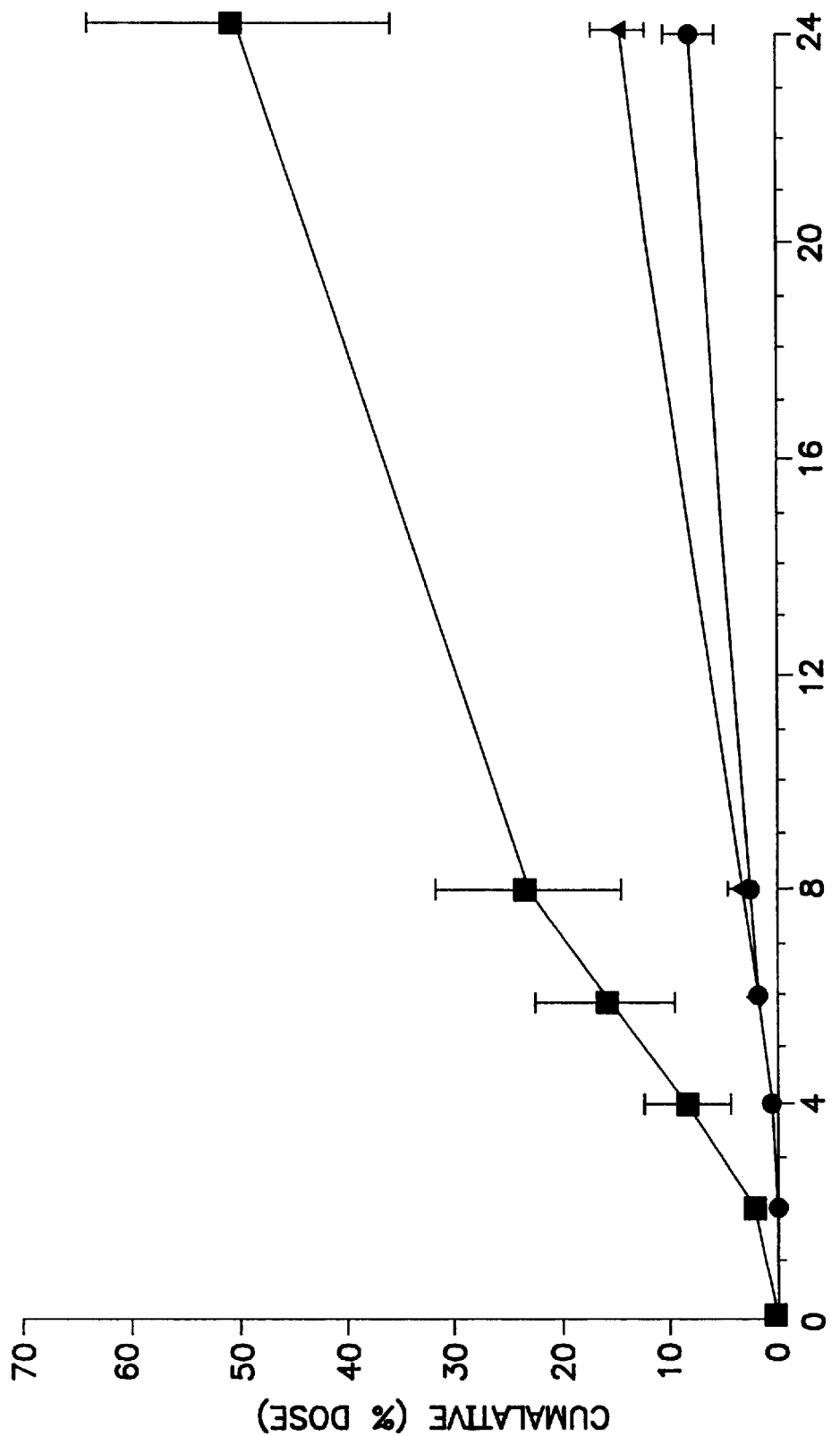
FIG. 5 is a graph plotting the cumulative delivery of testosterone through human skin versus time in vitro for two gel formulations; one according to the invention, non-occluded, containing 10 wt. % 2-NND (■) and the other being the gel contained within the commercially available Androderm® patch, placed under occlusion (▲) or without occlusion (●).

This example shows the effectiveness of the invention topical formulations for transdermal delivery of testosterone. In particular, this example shows the results for a topical aqueous alcoholic gel formulation according to the present invention for the transdermal delivery of testosterone in comparison to the gel formulation removed from a commercially available testosterone-containing patch (Androderm®). The topical gel according to the present invention contained 10 wt. % 2-NND and an ethanol/1,2-propylene glycol/water vehicle at a 70:20:10 ratio. The tests were run under the same conditions as described in Example 2 using each of the gels in equal amounts in terms of a finite dose of testosterone. An appropriate amount of gel was removed from the Androderm patch and used in the tests. The results for cumulative delivery of the patch formulation for 24 hours is calculated on the basis of 3.5 day delivery per patch. Although the patch is designed to meter the dose over the desired period (3.5 days) via an attenuating membrane, in the subject in vitro tests on human skin, the gel was applied without the membrane component of the patch. The results obtained from the static cell in vitro tests run under the same conditions as previously described are shown in FIG. 5. As can be readily seen from FIG. 5, the gel of the present invention is more efficient (higher percent delivery of testosterone) than the occluded and non-occluded gel of the Androderm commercial product.

What is claimed is:

1. An alcoholic or aqueous alcoholic topical composition for the transdermal delivery of a hormonally active drug which comprises, on a weight basis, of the total composition:

from about 0.1 to about 10% of hormonally active drug;

from about 2 to 20% of skin penetration enhancer comprising $C_7$ to $C_{14}$-hydrocarbyl substituted 1,3-dioxolane, 1,3-dioxane or acetal, wherein the hydrocarbyl group substituent has from about 7 to 10 carbon atoms;

0 to about 25% 1,2-propylene glycol;

from about 35 to 75% ethanol, isopropanol or mixture thereof;

0 to about 35% water; and, 0 to about 4% of cellulosic thickener.

2. The topical composition according to claim 1 which comprises on a weight basis:

from about 1 to about 6% of hormonally active drug;

from about 2 to 15% of said enhancer;

5 to about 22% 1,2-propylene glycol;

from about 40 to 75% ethanol, isopropanol or mixture thereof;

0 to about 25% water; and, 0 to about 3% of cellulosic thickener.

3. The topical composition according to claim 1 which comprises, on a weight basis:

from about 1.0 to about 4% of hormonally active drug;

from about 5 to 10% of said enhancer;

5 to about 20% 1,2-propylene glycol;

from about 50 to 75% ethanol, isopropanol or mixture thereof;

0 to about 25% water; and, 0 to about 2% of cellulosic thickener.

4. The topical composition according to claim 1 wherein the hormonally active drug is an estrogen, progesterone or androgen or mixture thereof.

5. The topical composition according to claim 4 wherein the hormonally active drug comprises testosterone.

6. The topical composition according to claim 4 wherein the hormonally active drug comprises an estradiol.

7. The topical composition according to claim 4 wherein the hormonally active drug comprises progesterone.

8. A method for the transdermal administration of hormonally active drug to a patient in need thereof which comprises topically applying to the skin of the patient an alcoholic or aqueous alcoholic composition comprising a therapeutically effective amount of hormonally active drug in a vehicle comprising a lower alcohol selected from the group consisting of ethanol, isopropanol and mixture thereof, 1,2-alkyl diol having from 3 to 6 carbon atoms, and water in a mixing ratio of alcohol:glycol:water of 50–80:5–20:5–40, said vehicle comprising from about 70 to 90 weight percent of the composition, and from about 5 to about 20 weight percent of a skin penetration enhancing compound selected from the group consisting of 2-hydrocarbyl-1,3-dioxolane, 2-hydrocarbyl-1,3-dioxane and hydrocarbyl substituted-acetal, wherein the hydrocarbyl group has from 7 to 14 carbon atoms.

9. The method for the transdermal administration of hormonally active drug according to claim 8 wherein the drug is selected from the group consisting of testosterone, progesterone and estradiol.

10. The topical composition according to claim 5 comprising an ethanol/propylene glycol/water carrier system at a weight ratio of 70:10–20:20–10; and about 10% by weight of 2-n-nonyl-1,3-dioxolane.

11. The topical composition according to claim 6 comprising an ethanol/propylene glycol/water carrier system at a weight ratio of 70:10–20:20–10; and from about 5 to about 10% by weight of 2-n-nonyl-1,3-dioxolane.

12. The topical composition according to claim 11 comprising about 10 percent by weight of 2-n-nonyl-1,3-dioxolane.

13. The topical composition according to claim 7 comprising an ethanol/propylene glycol/water carrier system at a weight ratio of 70:10–20:20–10; and from about 5 to about 10% by weight of 2-n-nonyl-1,3-dioxolane.

14. The topical composition according to claim 13 comprising about 10 percent by weight of 2-n-nonyl-1,3-dioxolane.

15. The method according to claim 8 wherein the hormonally active drug is testosterone.

16. The method according to claim 8 wherein the hormonally active drug is estradiol.

17. The method according to claim 8 wherein the hormonally active drug is progesterone.

* * * * *